United States Patent
Ryba et al.

(10) Patent No.: US 7,004,936 B2
(45) Date of Patent: Feb. 28, 2006

(54) REFRIGERATION SOURCE FOR A CRYOABLATION CATHETER

(75) Inventors: Eric Ryba, San Diego, CA (US); David J. Lentz, La Jolla, CA (US); Ravikumar Kudaravalli, Florence, SC (US)

(73) Assignee: CryoCor, Inc., San Diego, CA (US)

( * ) Notice: Subject to any disclaimer, the term of this patent is extended or adjusted under 35 U.S.C. 154(b) by 0 days.

(21) Appl. No.: 10/243,997

(22) Filed: Sep. 12, 2002
(Under 37 CFR 1.47)

(65) Prior Publication Data

US 2003/0220634 A1   Nov. 27, 2003

Related U.S. Application Data

(63) Continuation-in-part of application No. 09/635,108, filed on Aug. 9, 2000, now Pat. No. 6,471,694.

(51) Int. Cl.
*A61B 18/18* (2006.01)

(52) U.S. Cl. .............................. 606/20; 606/22; 606/24

(58) Field of Classification Search ............ 606/20–26; 62/293
See application file for complete search history.

(56) References Cited

U.S. PATENT DOCUMENTS

| | | |
|---|---|---|
| 3,696,813 A | 10/1972 | Wallach |
| 3,913,581 A | 10/1975 | Ritson et al. |
| 4,018,227 A | 4/1977 | Wallach |
| 5,139,496 A | 8/1992 | Hed |
| 5,147,355 A | 9/1992 | Friedman et al. |
| 5,281,213 A | 1/1994 | Milder et al. |
| 5,281,215 A | 1/1994 | Milder |
| 5,423,807 A | 6/1995 | Milder |
| 5,759,182 A | 6/1998 | Varney et al. |
| 5,876,399 A | 3/1999 | Chia et al. |
| 5,899,898 A | 5/1999 | Arless et al. |
| 5,899,899 A | 5/1999 | Arless et al. |
| 5,992,158 A | 11/1999 | Goddard et al. |
| 6,024,740 A | 2/2000 | Lesh et al. |
| 6,048,919 A | 4/2000 | McCullough |
| 6,117,101 A | 9/2000 | Diederich et al. |
| 6,139,544 A | 10/2000 | Mikus et al. |
| 6,235,019 B1 | 5/2001 | Lehmann et al. |
| 6,237,355 B1 | 5/2001 | Li |
| 6,245,064 B1 | 6/2001 | Lesh et al. |
| 6,251,105 B1 | 6/2001 | Mikus et al. |
| 6,280,439 B1 | 8/2001 | Martin et al. |
| 6,283,959 B1 | 9/2001 | Lalonde et al. |
| 6,383,180 B1 * | 5/2002 | Lalonde et al. ............... 606/22 |
| 6,407,149 B1 | 6/2002 | McCullough |

(Continued)

FOREIGN PATENT DOCUMENTS

CA           1337791        12/1995

(Continued)

*Primary Examiner*—Rosiland Rollins
(74) *Attorney, Agent, or Firm*—Nydegger & Associates

(57) ABSTRACT

A catheter-based system for performing a cryoablation procedure uses a precooler to lower the temperature of a fluid refrigerant to a sub-cool temperature (−40° C.) at a working pressure (400 psi). The sub-cooled fluid is then introduced into a supply line of the catheter. Upon outflow of the primary fluid from the supply line, and into a tip section of the catheter, the fluid refrigerant boils at an outflow pressure of approximately one atmosphere, at a temperature of about −88° C. In operation, the working pressure is computer controlled to obtain an appropriate outflow pressure for the coldest possible temperature in the tip section.

17 Claims, 3 Drawing Sheets

U.S. PATENT DOCUMENTS

| | | | |
|---|---|---|---|
| 6,468,268 B1 | 10/2002 | Abboud et al. |
| 6,471,693 B1 | 10/2002 | Carroll et al. |
| 6,527,769 B1 | 3/2003 | Langberg et al. |
| 6,540,740 B1 | 4/2003 | Lehmann et al. |
| 6,562,030 B1 | 5/2003 | Abboud et al. |
| 6,569,158 B1 | 5/2003 | Abboud et al. |
| 6,575,933 B1 | 6/2003 | Wittenberger et al. |
| 6,575,966 B1 | 6/2003 | Lane et al. |
| 6,579,287 B1 | 6/2003 | Wittenberger et al. |
| 6,585,717 B1 | 7/2003 | Wittenberger et al. |
| 6,585,728 B1 | 7/2003 | Heiner et al. |
| 6,585,729 B1 | 7/2003 | Eum |
| 6,589,234 B1 | 7/2003 | Lalonde et al. |
| 6,592,577 B1 | 7/2003 | Abboud et al. |
| 6,595,988 B1 | 7/2003 | Wittenberger et al. |
| 6,602,247 B1 | 8/2003 | Lalonde |
| 6,605,087 B1 | 8/2003 | Swartz et al. |
| 6,629,972 B1 | 10/2003 | Lehmann et al. |
| 6,635,053 B1 | 10/2003 | Lalonde et al. |
| 6,733,494 B1 | 5/2004 | Abboud et al. |
| 6,755,823 B1 | 6/2004 | Lalonde |
| 6,761,714 B1 | 7/2004 | Abboud et al. |
| 2001/0021847 A1 | 9/2001 | Abboud et al. |
| 2001/0025075 A1 | 9/2001 | Smith et al. |
| 2002/0025998 A1 | 2/2002 | McCullough et al. |
| 2002/0062122 A1 | 5/2002 | Lehmann et al. |
| 2002/0111612 A1 | 8/2002 | Lalonde et al. |
| 2002/0115989 A1 | 8/2002 | Abboud et al. |
| 2003/0004504 A1 | 1/2003 | Abboud et al. |
| 2003/0009160 A1 | 1/2003 | Carroll et al. |
| 2003/0018326 A1 | 1/2003 | Abboud et al. |
| 2003/0097124 A1 | 5/2003 | Lehmann et al. |
| 2004/0049187 A1 | 3/2004 | Abboud et al. |
| 2004/0054361 A1 | 3/2004 | Lehmann et al. |

FOREIGN PATENT DOCUMENTS

| | | |
|---|---|---|
| WO | WO 90/03151 | 4/1990 |
| WO | WO 02/11638 A1 | 2/2002 |
| WO | WO 02/058576 A1 | 8/2002 |

* cited by examiner

REFRIGERATION SOURCE FOR A CRYOABLATION CATHETER

This application is a continuation-in-part of application Ser. No. 09/635,108 filed Aug. 9, 2000, now U.S. Pat. No. 6,471,694. The contents of application Ser. No. 09/635,108 are incorporated herein by reference.

FIELD OF THE INVENTION

The present invention pertains generally to systems and methods for implementing cryoablation procedures. More particularly, the present invention pertains to systems and methods that precool a primary fluid to a sub-cooled, fully saturated liquid state, for use in a cryoablation procedure. The present invention is particularly, but not exclusively, useful as a system and method for cooling the distal tip of a cryoablation catheter during cardiac cryoablation therapy to cure heart arrhythmias.

BACKGROUND OF THE INVENTION

As the word itself indicates, "cryoablation" involves the freezing of material. Of importance here, at least insofar as the present invention is concerned, is the fact that cryoablation has been successfully used in various medical procedures. In this context, it has been determined that cryoablation procedures can be particularly effective for curing heart arrhythmias, such as atrial fibrillation.

It is believed that at least one-third of all atrial fibrillations originate near the ostia of the pulmonary veins, and that the optimal treatment technique is to treat these focal areas through the creation of circumferential lesions around the ostia of these veins. Heretofore, the standard ablation platform has been radiofrequency energy. Radiofrequency energy, however, is not amenable to safely producing circumferential lesions without the potential for serious complications. Specifically, while ablating the myocardial cells, heating energy also alters the extracellular matrix proteins, causing the matrix to collapse. This may be the center of pulmonary vein stenosis. Moreover, radiofrequency energy is known to damage the lining of the heart, which may account for thromboembolic complications, including stroke. Cryoablation procedures, however, may avoid many of these problems.

In a medical procedure, cryoablation begins at temperatures below approximately minus twenty degrees Centigrade (−20° C.). For the effective cryoablation of tissue, however, much colder temperatures are preferable. With this goal in mind, various fluid refrigerants (e.g. nitrous oxide $N_2O$), which have normal boiling point temperatures as low as around minus eighty eight degrees Centigrade (−88° C.), are worthy of consideration. For purposes of the present invention, the normal boiling point temperature of a fluid is taken to be the temperature at which the fluid boils under one atmosphere of pressure. Temperature alone, however, is not the goal. Specifically, it is also necessary there be a sufficient refrigeration potential for freezing the tissue. In order for a system to attain and maintain a temperature, while providing the necessary refrigeration potential to effect cryoablation of tissue, several physical factors need to be considered. Specifically, these factors involve the thermodynamics of heat transfer.

It is well known that when a fluid boils (i.e. changes from a liquid state to a gaseous state) a significant amount of heat is transferred to the fluid. With this in mind, consider a liquid that is not boiling, but which is under a condition of pressure and temperature wherein effective evaporation of the liquid ceases. A liquid in such condition is commonly referred to as being "fully saturated". It will then happen, as the pressure on the saturated liquid is reduced, the liquid tends to boil and extract heat from its surroundings. Initially, the heat that is transferred to the fluid is generally referred to as latent heat. More specifically, this latent heat is the heat that is required to change a fluid from a liquid to a gas, without any change in temperature. For most fluids, this latent heat transfer can be considerable and is subsumed in the notion of wattage. In context, wattage is the refrigeration potential of a system. Stated differently, wattage is the capacity of a system to extract energy at a fixed temperature.

An important consideration for the design of any refrigeration system is the fact that heat transfer is proportional to the difference in temperatures ($\Delta T$) between the refrigerant and the body that is being cooled. Importantly, heat transfer is also proportional to the amount of surface area of the body being cooled (A) that is in contact with the refrigerant. In addition to the above considerations (i.e. $\Delta T$ and A); when the refrigerant is a fluid, the refrigeration potential of the refrigerant fluid is also a function of its mass flow rate. Specifically, the faster a heat-exchanging fluid refrigerant can be replaced (i.e. the higher its mass flow rate), the higher will be the refrigeration potential. This notion, however, has it limits.

As is well known, the mass flow rate of a fluid results from a pressure differential on the fluid. More specifically, it can be shown that as a pressure differential starts to increase on a refrigerant fluid in a system, the resultant increase in the mass flow rate of the fluid will also increase the refrigeration potential of the system. This increased flow rate, however, creates additional increases in the return pressure that will result in a detrimental increase in temperature. As is also well understood by the skilled artisan, this effect is caused by a phenomenon commonly referred to as "back pressure." Obviously, an optimal operation occurs with the highest mass flow rate at the lowest possible temperature.

In light of the above, it is an object of the present invention to provide an open-cycle, or closed-cycle, refrigeration system for cooling the tip of a cryoablation catheter that provides a pre-cooling stage in the system to maximize the refrigeration potential of the refrigerant fluid at the tip of the catheter. Another object of the present invention is to provide a refrigeration system for cooling the tip of a cryoablation catheter that substantially maintains a predetermined pressure at the tip of the catheter to maximize the refrigeration potential of the refrigerant fluid at the tip. Still another object of the present invention is to provide a refrigeration system for cooling the tip of a cryoablation catheter that provides the maximum practical surface area for the tip that will maximize the ablation potential of the refrigerant fluid. Also, it is an object of the present invention to provide a refrigeration system for cooling the tip of a cryoablation catheter that is relatively easy to manufacture, is simple to use, and is comparatively cost effective.

SUMMARY OF THE PREFERRED EMBODIMENTS

A refrigeration system (open-cycle, or closed-cycle) for cooling the tip of a cryoablation catheter includes a source for a primary fluid refrigerant, such as nitrous oxide ($N_2O$). Initially, the primary fluid is held under pressure (e.g. 750 psia) at ambient temperature (e.g. room temperature). A pressure regulator is connected in fluid communication with the primary fluid source for reducing the pressure on the primary fluid down to a working pressure (e.g. approximately 400 psia). During this pressure reduction to the working pressure, the primary fluid remains at substantially the ambient temperature.

After pressure on the primary fluid has been reduced to the working pressure, a precooler is used to pre-cool the primary fluid from the ambient temperature. This is done while substantially maintaining the primary fluid at the working pressure. Importantly, at the precooler, the primary fluid is converted into a fully saturated liquid which has been pre-cooled to a sub-cool temperature. As used here, a sub-cool temperature is one that is below the temperature at which, for a given pressure, the fluid becomes fully saturated. For example, when nitrous oxide is to be used, the preferred sub-cool temperature will be equal to approximately minus forty degrees Centigrade ($T_{sc}=-40°$ C.).

Structurally, the precooler is preferably a closed-cycle refrigeration unit that includes an enclosed secondary fluid (e.g. a freon gas). Additionally, the precooler includes a compressor for increasing the pressure on the secondary fluid to a point where the secondary fluid becomes a liquid. Importantly, for whatever secondary fluid is used, it should have a normal boiling point that is near to the preferred sub-cool temperature of the primary fluid ($T_{sc}$). The secondary fluid is then allowed to boil, and to thereby pre-cool the primary fluid in the system to its sub-cool temperature ($T_{sc}$). As a closed-cycle unit, the secondary fluid is recycled after it has pre-cooled the primary fluid.

The cryoablation catheter for the system of the present invention essentially includes a capillary tube that is connected with, and extends coaxially from a supply tube. Together, the connected supply and capillary tubes are positioned in the lumen of a catheter tube and are oriented coaxially with the catheter tube. More specifically, the supply tube and the capillary tube each have a distal end and a proximal end and, in combination, the proximal end of the capillary tube is connected to the distal end of the supply tube to establish a supply line for the catheter.

For the construction of the cryoablation catheter, the supply tube and the capillary tube are concentrically (coaxially) positioned inside the lumen of the catheter tube. Further, the distal end of the capillary tube (i.e. the distal end of the supply line) is positioned at a closed-in tip section at the distal end of the catheter tube. Thus, in addition to the supply line, this configuration also defines a return line in the lumen of the catheter tube that is located between the inside surface of that catheter tube and the supply line. In particular, the return line extends from the tip section at the distal end of the catheter tube, back to the proximal end of the catheter tube.

Insofar as the supply line is concerned, it is an important aspect of the present invention that the impedance to fluid flow of the primary refrigerant in the supply line be relatively low through the supply tube, as compared with the impedance presented by the capillary tube. Stated differently, it is desirable for the pressure drop, and consequently the temperature reduction, on the primary refrigerant be minimized as it traverses the supply tube. On the other hand, the pressure drop and temperature reduction on the primary refrigerant should be maximized as the refrigerant traverses the capillary tube. Importantly, the physical dimensions of the supply tube, of the capillary tube, and of the catheter tube can be engineered to satisfy these requirements. It is also desirable to engineer the length of the capillary tube so that gases passing from the tip section, back through the return line do not impermissibly warm the capillary tube. By balancing these considerations, the dimensions of the supply line, the tip section and the return line, can all be predetermined.

As the fluid refrigerant is transferred from its source to the catheter supply line, it passes through the precooler. During this transfer, a control valve(s) is used to establish a working pressure ($p_w$) for the refrigerant. Also, a pressure sensor is provided to monitor the working pressure on the primary fluid refrigerant before the refrigerant enters the supply line at the proximal end of the catheter.

On the return side of the system, an exhaust unit is provided for removing the primary fluid from the tip section of the catheter. For the present invention, this exhaust unit consists of a vacuum pump that is attached in fluid communication with the return line at the proximal end of the catheter tube. A pressure sensor is also provided at this point to determine the pressure in the return line at the proximal end of the catheter tube ($p_r$).

In accordance with well known thermodynamic principles, when pressures at specific points in a system are known, fluid pressures at various other points in the system can be determined. For the present invention, because the supply line and return line are contiguous and have known dimensions, because "$p_w$" (working pressure) and "$p_r$" (return line pressure) can be determined and, further, because the fluid refrigerant experiences a phase change during the transition from $p_w$ to $p_r$, it is possible to calculate pressures on the fluid refrigerant at points between the proximal end of the supply tube (inlet) and the proximal end of the catheter tube (outlet). In particular, it is possible to calculate an outflow pressure ($p_o$) for the fluid refrigerant as it exits from the distal end of the capillary tube into the tip section of the catheter.

The outflow pressure ($p_o$) for the fluid refrigerant can be determined in ways other than as just mentioned above. For one, a pressure sensor can be positioned in the tip section of the catheter near the distal end of the capillary tube to measure the outflow pressure ($p_o$) directly. Additionally, the system of the present invention can include a temperature sensor that is positioned in the tip section of the catheter to monitor the temperature of the primary fluid refrigerant in the tip section ($T_t$). Specifically, when this temperature ($T_t$) is measured as the primary fluid refrigerant is boiling (i.e. as it enters the tip section from the capillary tube), it is possible to directly calculate the outflow pressure ($p_o$) using well known thermodynamic relationships.

A computer is used with the system of the present invention to monitor and control the operational conditions of the system. Specifically, the computer is connected to the appropriate sensors that monitor actual values for "$p_r$" and "$p_w$". The values for "$p_r$" and "$p_w$" can then be used to determine the outflow pressure "$p_o$" in the tip section of the catheter (for one embodiment of the present invention, "$p_o$" is also measured directly). Further, the computer is connected to the control valve to manipulate the control valve and vary the working pressure ($p_w$) on the primary fluid. At the same time, the computer can monitor the temperature in the tip section of the catheter ($T_t$) to ensure that changes in the working pressure "$p_w$" result in appropriate changes in "$T_t$". Stated differently, the computer can monitor conditions to ensure that an unwanted increase in "back pressure," that would be caused by an inappropriate increase in "$p_w$" does not result in an increase in "$T_t$". The purpose here is to maintain the outflow pressure ($p_o$) in the tip section of the catheter at a desired value (e.g. 15 psia).

In operation, the sub-cooled primary fluid is introduced into the proximal end of the capillary tube at substantially the working pressure ($p_w$). The primary fluid then traverses the capillary tube for outflow from the distal end of the capillary tube at the outflow pressure ($p_o$). Importantly, in the capillary tube the fluid refrigerant is subjected to a pressure differential ($\Delta p$). In this case, "$\Delta p$" is substantially the difference between the working pressure ($p_w$) on the primary fluid as it enters the proximal end of the capillary tube (e.g. 300 psi), and a substantially ambient pressure (i.e. $p_o$) as it outflows from the distal end of the capillary tube (e.g. one atmosphere, 15 psi) ($\Delta p = p_w - p_o$). In particular, as the pre-cooled primary fluid passes through the capillary tube, it transitions from a sub-cool temperature that is equal to approximately minus forty degrees Centigrade ($T_{sc} \cong -40°$ C.), to approximately its normal boiling point temperature. As defined above, the normal boiling point temperature of a fluid is taken to be the temperature at which the fluid boils under one atmosphere of pressures. In the case of nitrous oxide, this will be a cryoablation temperature that is equal to approximately minus eighty-eight degrees Centigrade ($T_{ca} \cong -88°$ C.). The heat that is absorbed by the primary fluid as it boils, cools the tip section of the catheter.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENT

Figure 1:
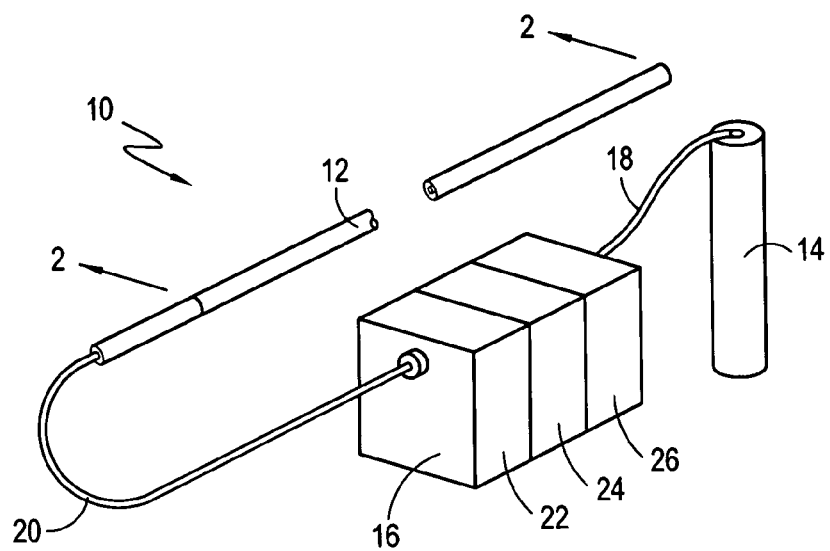
FIG. 1 is a perspective view of the system of the present invention.

Referring initially to FIG. 1, a system for a performing cryoablation procedures is shown and generally designated 10. As shown, the system 10 includes a cryoablation catheter 12 and a primary fluid source 14. Preferably, the primary fluid is nitrous oxide ($N_2O$) and is held in source 14 at a pressure of around 750 psig. FIG. 1 also shows that the system 10 includes a console 16 and that the console 16 is connected in fluid communication with the primary fluid source 14 via a fluid line 18. Console 16 is also connected in fluid communication with the catheter 12 via a fluid line 20. Further, the console 16 is shown to include a precooler 22, an exhaust unit 24, and a computer 26.

Figure 2:
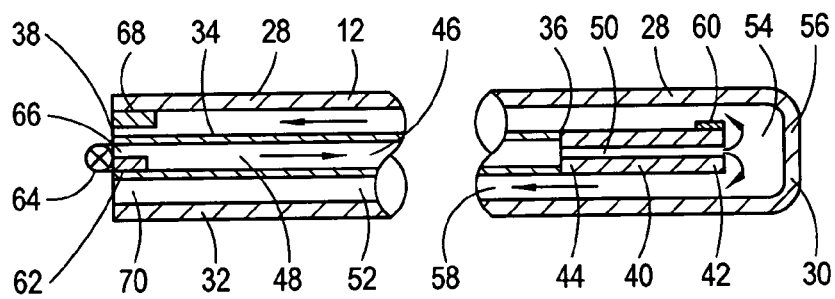
FIG. 2 is a cross-sectional view of the catheter of the present invention as seen along the line 2—2 in FIG. 1.

In detail, the components of the catheter 12 will be best appreciated with reference to FIG. 2. There, it will be seen that the catheter 12 includes a catheter tube 28 that has a closed distal end 30 and an open proximal end 32. Also included as part of the catheter 12, are a supply tube 34 that has a distal end 36 and a proximal end 38, and a capillary tube 40 that has a distal end 42 and a proximal end 44. As shown, the distal end 36 of supply tube 34 is connected with the proximal end 44 of the capillary tube 40 to establish a supply line 46. Specifically, supply line 46 is defined by the lumen 48 of supply tube 34 and the lumen 50 of capillary tube 40. It is an important aspect of the system 10 that the diameter (i.e. cross section) of the supply tube 34 is greater than the diameter (i.e. cross section) of the capillary tube 40. The consequence of this difference is that the supply tube 34 presents much less impedance to fluid flow than does the capillary tube 40. In turn, this causes a much greater pressure drop for fluid flow through the capillary tube 40. As will be seen, this pressure differential is used to advantage for the system 10.

Still referring to FIG. 2, it is seen that the supply line 46 established by the supply tube 34 and capillary tube 40, is positioned coaxially in the lumen 52 of the catheter tube 28. Further, the distal end 42 of the capillary tube 40 (i.e. also the distal end of the supply line 46) is displaced from the distal end 30 of catheter tube 28 to create an expansion chamber 54 in the tip section 56 of the catheter 12. Additionally, the placement of the supply line 46 in the lumen 52 establishes a return line 58 in the catheter 12 that is located between the supply line 46 and the wall of the catheter tube 28.

Optionally, a sensor 60 can be mounted in expansion chamber 54 (tip section 56). This sensor 60 may be either a temperature sensor or a pressure sensor, or it may include both a temperature and pressure sensor. In any event, if used, the sensor 60 can be of a type well known in the art for detecting the desired measurement. Although FIG. 2 shows both a pressure sensor 62 and a valve 64 positioned at the proximal end 38 of the supply tube 34, this is only exemplary as the sensor 62 and valve 64 may actually be positioned elsewhere. The import here is that a pressure sensor 62 is provided to monitor a working fluid pressure, "$p_w$," on a fluid refrigerant (e.g. $N_2O$). In turn, this pressure "$p_w$" is controlled by a valve 64 as it enters the inlet 66 of the supply line 46. Further, FIG. 2 shows that a pressure sensor 68 is provided to monitor a return pressure "$p_r$" on the fluid refrigerant as it exits from the outlet 70 of the return line 58.

Figure 3:
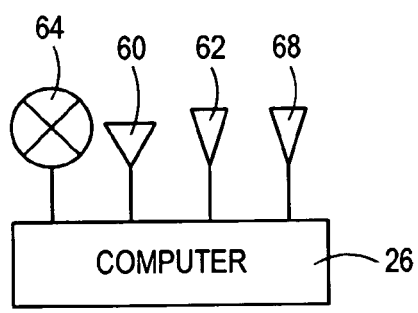
FIG. 3 is a schematic view of the computer and its interaction with system components and sensors for use in the control of a cryoablation procedure.

FIG. 3 indicates that the various sensors mentioned above are somehow electronically connected to the computer 26 in console 16. More specifically, the sensors 60, 62 and 68 can be connected to computer 26 in any of several ways, all known in the pertinent art. Further, FIG. 3 indicates that the computer 26 is operationally connected with the valve 64. The consequence of this is that the computer 26 can be used to control operation of the valve 64, and thus the working pressure "$p_w$", in accordance with preprogrammed instructions, using measurements obtained by the sensors 60, 62 and 68 (individually or collectively).

Figure 4:
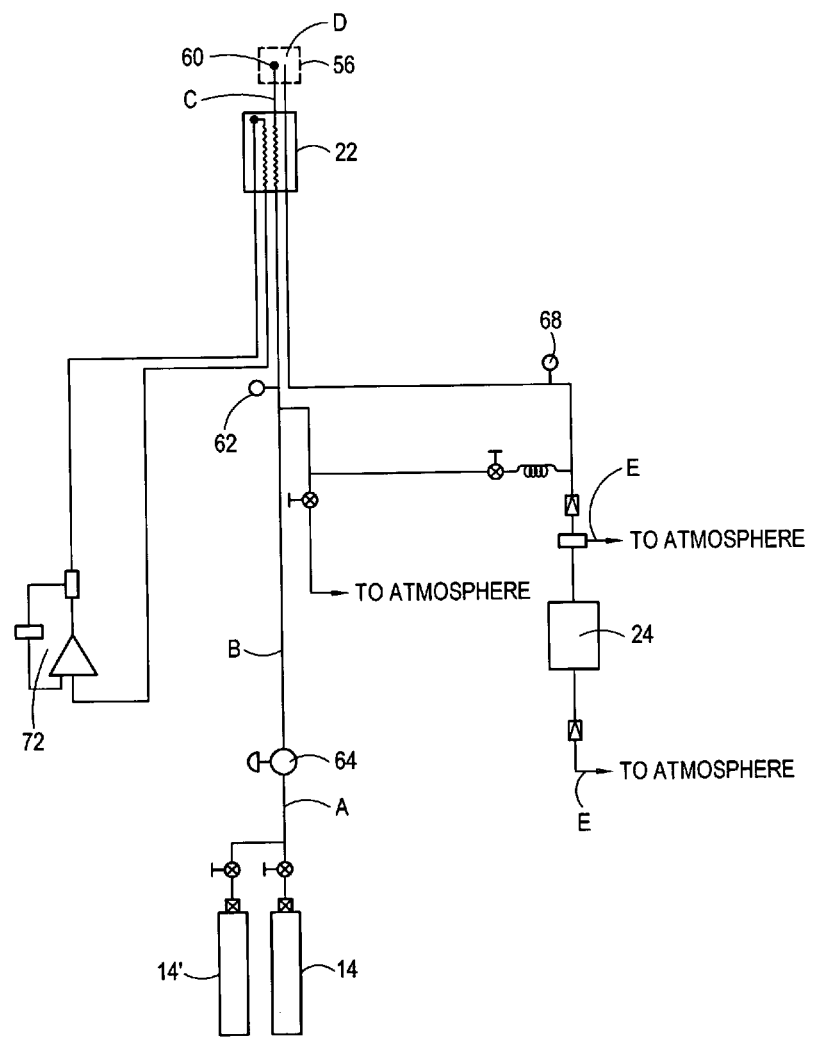
FIG. 4 is a schematic view of the interactive components in the console of the present invention.

A schematic of various components for system 10 is presented in FIG. 4 which indicates that a compressor 72 is incorporated as an integral part of the precooler 22. More specifically, the compressor 72 is used to compress a secondary fluid refrigerant (e.g. Freon) into its liquid phase for subsequent cooling of the primary refrigerant in the precooler 22. For purposes of the present invention, the secondary fluid refrigerant will have a normal boiling point that is at a temperature sufficiently low to take the primary fluid refrigerant to a sub-cool condition (i.e. below a temperature where the primary fluid refrigerant will be fully saturated). For the present invention, wherein the primary fluid refrigerant is nitrous oxide, the temperature is preferably around minus forty degrees Centigrade ($T_{sc}$=−40° C.).

Figure 5:
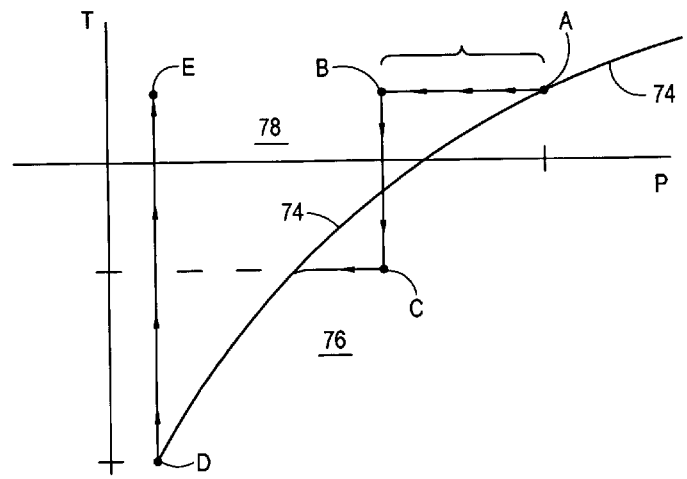
FIG. 5 is a pressure-temperature diagram (not to scale) graphing an open-cycle operation for a refrigerant fluid in accordance with the present invention.

The operation of system 10 will be best appreciated by cross referencing FIG. 4 with FIG. 5. During this cross referencing, recognize that the alphabetical points (A, B, C, D and E), shown relative to the curve 74 in FIG. 5, are correspondingly shown on the schematic for system 10 in FIG. 4. Further, appreciate that curve 74, which is plotted for variations of pressure (P) and temperature (T), represents the fully saturated condition for the primary fluid refrigerant (e.g. nitrous oxide). Accordingly, the area 76 represents the liquid phase of the refrigerant, and area 78 represents the gaseous phase of the refrigerant.

Point A (FIG. 4 and FIG. 5) represents the primary fluid refrigerant as it is drawn from the fluid source 14, or its back up source 14'. Preferably, point A corresponds to ambient temperature (i.e. room temperature) and a pressure greater than around 700 psig. After leaving the fluid source 14, the pressure on the refrigerant is lowered to a working pressure "$p_w$" that is around 400 psig. This change is controlled by the regulator valve 64, is monitored by the sensor 62, and is represented in FIG. 5 as the change from point A to point B. The condition at point B corresponds to the condition of the primary refrigerant as it enters the precooler 22.

In the precooler 22, the primary refrigerant is cooled to a sub-cool temperature "$T_{sc}$" (e.g. −40° C.) that is determined by the boiling point of the secondary refrigerant in the precooler 22. In FIG. 5 this cooling is represented by the transition from point B to point C. Note that in this transition, as the primary fluid refrigerant passes through the precooler 22, it changes from a gaseous state (area 78) into a liquid state (area 76). Point C in FIG. 5 represents the condition of the primary fluid refrigerant as it enters the supply line 46 of cryocatheter 12 at the proximal end 38 of supply tube 34. Specifically, the pressure on the primary fluid refrigerant at this point C is the working pressure "$p_w$", and the temperature is the sub-cool temperature "$T_{sc}$".

As the primary fluid refrigerant passes through the supply line 46 of catheter 12, its condition changes from the indications of point C, to those of point D. Specifically, for the present invention, point D is identified by a temperature of around minus eighty eight degrees Centigrade (−88° C.) and an outlet pressure "$p_o$" that is close to 15 psia. Further, as indicated in FIG. 4, point D identifies the conditions of the primary fluid refrigerant after it has boiled in the tip section 56 as it is leaving the supply line 46 and entering the return line 58 of the catheter 12.

The exhaust unit 24 of the catheter 12 is used to evacuate the primary fluid refrigerant from the expansion chamber 54 of tip section 56 after the primary refrigerant has boiled. During this evacuation, the conditions of the primary refrigerant change from point D to point E. Specifically, the conditions at point E are such that the temperature of the refrigerant is an ambient temperature (i.e. room temperature) and it has a return pressure "$p_r$", measured by the sensor 68, that is slightly less than "$p_o$". For the transition from point D to point E, the main purpose of the exhaust unit 24 is to help maintain the outlet pressure "$p_o$" in the tip section 56 as near to one atmosphere pressure as possible.

Figure 6:
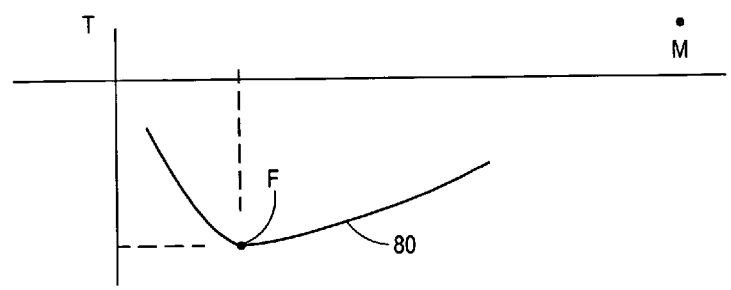
FIG. 6 is a diagram (not to scale) showing the tendency for changes in temperature response to changes of fluid mass flow rate in a catheter environment as provided by the present invention.

Earlier it was mentioned that the mass flow rate of the primary fluid refrigerant as it passes through the catheter 12 has an effect on the operation of the catheter 12. Essentially this effect is shown in FIG. 6. There it will be seen that for relatively low mass flow rates (e.g. below point F on curve 80 shown in FIG. 6), increases in the mass flow rate of the refrigerant will cause lower temperatures. Refrigerant flow in this range is said to be "refrigeration limited." On the other hand, for relatively high mass flow rates (i.e. above point F), increases in the mass flow rate actually cause the temperature of the refrigerant to rise. Flow in this range is said to be "surface area limited." Because the system 10 is most efficient at the lowest temperature for the refrigerant, operation at point F is preferred. Accordingly, by monitoring the temperature of the refrigerant in the tip section 56, "$T_t$", variations of $T_t$ can be used to control the mass flow rate of the refrigerant, to thereby control the refrigeration potential of the catheter 12.

In operation, the variables mentioned above ($p_w$, $p_o$, $p_r$, and $T_t$) can be determined as needed. System 10 then manipulates the regulator valve 64, in response to whatever variables are being used, to vary the working pressure "$p_w$" of the primary fluid refrigerant as it enters the supply line 46. In this way, variations in "$p_w$" can be used to control "$p_o$" and, consequently, the refrigeration potential of the catheter 12.

While the particular Refrigeration Source for a Cryoablation Catheter as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A refrigeration system for cooling a tip section of a cryoablation catheter which comprises:

a source for a primary fluid refrigerant wherein the primary fluid refrigerant is nitrous oxide ($N_2O$);

a closed-cycle refrigeration unit for pre-cooling the primary fluid to a sub-cool temperature ($T_{sc}$) at a working pressure ($p_w$) wherein the sub-cool temperature is approximately minus forty degrees Centigrade ($T_{sc}$=−40° C.) and the working pressure is approximately four hundred psia;

a catheter tube formed with a lumen and having an open proximal end and a closed distal end, with the closed distal end of said catheter tube defining a tip section;

a supply line having a distal end and a proximal end, said supply line being positioned inside the lumen of the catheter tube with the distal end thereof positioned in the tip section of said catheter tube, wherein said supply line includes a supply tube and a coaxial capillary tube extending distally therefrom, and further wherein said capillary tube has a fluid flow impedance greater than a fluid flow impedance of said supply tube;

a means for introducing the sub-cooled primary fluid into the proximal end of said capillary tube at approximately −40° C. and at substantially the working pressure ($p_w$) for transfer therethrough and outflow therefrom into the tip section of said catheter tube in a substantially liquid state at approximately −88° C. and at an outflow pressure ($p_o$); and a vacuum means connected in fluid communication with the proximal end of said catheter tube for removing the primary fluid therefrom at a return pressure ($p_r$), while maintaining the outflow pressure ($p_o$) in the tip section substantially at a predetermined value to allow the primary fluid to boil in the tip section substantially at its normal boiling point of approximately minus eighty eight degrees Centigrade.

2. A system as recited in claim 1 further comprising:

a first pressure sensor for measuring the working pressure ($p_w$) at the proximal end of the catheter tube;

a second pressure sensor for measuring the return pressure ($p_r$) at the proximal end of the catheter tube; and a computer for using the working pressure ($p_w$) and the return pressure ($p_r$) to calculate the outflow pressure ($p_o$) in the tip section.

3. A system as recited in claim 2 further comprising:

a regulator valve for varying the working pressure ($p_w$) on the primary fluid; and an electronic means connecting said computer to said regulator valve, wherein said computer compares the calculated outflow pressure ($p_o$) in the tip section to a base line pressure to create an error signal, and further wherein said computer adjusts said regulator valve to minimize the error signal for controlling the working pressure ($p_w$) to substantially maintain the outflow pressure ($p_o$) at the predetermined value.

4. A system as recited in claim 3 further comprising a temperature sensor mounted in the tip section to determine a tip section temperature ($T_t$), wherein said computer monitors the tip section temperature ($T_t$) to ensure appropriate control over the working pressure ($p_w$).

5. A system as recited in claim 1 wherein said closed-cycle refrigeration unit comprises:

a secondary fluid wherein the secondary fluid is a Freon;

a compressor for increasing pressure on the secondary fluid to convert the secondary fluid into a liquid having a boiling point equal to a sub-cool temperature of the primary fluid;

a means for boiling the secondary fluid to sub-cool the primary fluid to its sub-cool temperature; and a means for recycling the secondary fluid after the secondary fluid has sub-cooled the primary fluid.

6. A system as recited in claim 1 wherein the outflow pressure ($p_o$) is approximately fifteen psia ($p_o$=15 psia).

7. A system as recited in claim 1 wherein the supply tube has a proximal end and a distal end and the capillary tube has a proximal end and a distal end, wherein the distal end of the supply tube is connected with the proximal end of the capillary tube, wherein said supply line is coaxially positioned in the lumen of said catheter tube, and wherein said supply tube has a lumen with a diameter and said capillary tube has a lumen with a diameter, with the diameter of said supply tube being greater than the diameter of said capillary tube.

8. A system as recited in claim 1 further comprising a pressure sensor positioned in said tip section for measuring the outlet pressure ($p_o$).

9. A method for cooling a tip section of a cryoablation catheter which comprises the steps of:

providing a catheter tube formed with a lumen and having an open proximal end and a closed distal end, with the closed distal end of the catheter tube defining a tip section;

mounting a supply line inside the lumen of the catheter tube, the supply line having a distal end and a proximal end, with the distal end thereof positioned in the tip section of said catheter tube, wherein said supply line includes a supply tube and a coaxial capillary tube extending distally therefrom, and further wherein said capillary tube has a fluid flow impedance greater than a fluid flow impedance of said supply tube;

pre-cooling a primary fluid with a closed cycle refrigeration unit to a sub-cooled liquid state at a working pressure ($p_w$) wherein the primary fluid refrigerant is nitrous oxide ($N_2O$) and wherein the sub-cool temperature is approximately minus forty degrees Centigrade ($T_{sc}$=−40° C.) and the working pressure is approximately four hundred psia;

introducing the sub-cooled primary fluid into the proximal end of the capillary tube at approximately −40° C. and at substantially the working pressure ($p_w$) for transfer therethrough and outflow therefrom into the tip section of the catheter tube in a substantially liquid state at approximately −88° C. and at an outflow pressure ($p_o$);

removing the primary fluid from the proximal end of said catheter tube at a return pressure ($p_r$); and maintaining the outflow pressure ($p_o$) in the tip section substantially at a predetermined value to allow the primary fluid to boil in the tip section substantially at its normal boiling point of approximately minus eighty eight degrees Centigrade.

10. A method as recited in claim 9 further comprising the steps of:

measuring the working pressure ($p_w$) at the proximal end of the supply line;

measuring the return pressure ($p_r$) at the proximal end of the catheter tube; and calculating the outflow pressure ($p_o$) in the tip section based on the measured working pressure ($p_w$) and the measured return pressure ($p_r$).

11. A method as recited in claim 10 further comprising the steps of:

providing a control valve to vary the working pressure ($p_w$) on the primary fluid;

comparing the calculated outflow pressure ($p_o$) in the tip section to a base line pressure to create an error signal; and adjusting the control valve to minimize the error signal for controlling the working pressure ($p_w$) to substantially maintain the outflow pressure ($p_o$) at the predetermined value.

12. A method as recited in claim 11 wherein the pre-cooling step comprises:

increasing pressure on a secondary fluid to convert the secondary fluid into a liquid having a boiling point equal to a sub-cool temperature of the primary fluid; and boiling the secondary fluid to sub-cool the primary fluid to its sub-cool temperature.

13. A method as recited in claim 12 further comprising the steps of:

placing a temperature sensor in the tip section to determine a tip section temperature ($T_t$); and monitoring the tip section temperature ($T_t$) to ensure appropriate control over the working pressure ($p_w$).

14. A method as recited in claim 9 wherein the supply tube has a proximal end and a distal end and the capillary tube has a proximal end and a distal end and said method further comprises the step of connecting the distal end of the supply tube to the proximal end of the capillary tube to create said supply line.

15. A method as recited in claim 14 further comprising the steps of:

forming said supply tube with a lumen having a diameter; and forming said capillary tube with a lumen having a diameter, wherein the diameter of said supply tube being greater than the diameter of said capillary tube.

16. A method as recited in claim 15 further comprising the step of positioning a pressure sensor in said tip section for measuring the outlet pressure ($p_o$).

17. A method as recited in claim 15 further comprising the step of:
   positioning a temperature sensor in said tip section for measuring the tip temperature ($T_t$); and
   using the tip temperature ($T_t$) to calculate the outflow pressure ($p_O$).

* * * * *

UNITED STATES PATENT AND TRADEMARK OFFICE
CERTIFICATE OF CORRECTION

PATENT NO. : 7,004,936 B2
DATED : February 28, 2006
INVENTOR(S) : Ryba et al.

It is certified that error appears in the above-identified patent and that said Letters Patent is hereby corrected as shown below:

Column 10,
Line 31, delete "oufflow" insert -- outflow --.

Signed and Sealed this

Twenty-third Day of May, 2006

JON W. DUDAS
*Director of the United States Patent and Trademark Office*